United States Patent
Hu et al.

(10) Patent No.: US 9,592,086 B2
(45) Date of Patent: Mar. 14, 2017

(54) ELECTRODES FOR TISSUE TREATMENT

(71) Applicant: Boston Scientific Scimed, Inc., Maple Grove, MN (US)

(72) Inventors: Eric Y. Hu, San Jose, CA (US); Noah Webster, San Francisco, CA (US); Timothy R. Dalbec, Saratoga, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 740 days.

(21) Appl. No.: 13/895,023

(22) Filed: May 15, 2013

(65) Prior Publication Data

US 2014/0031816 A1 Jan. 30, 2014

Related U.S. Application Data

(60) Provisional application No. 61/675,244, filed on Jul. 24, 2012.

(51) Int. Cl.
*A61B 18/08* (2006.01)
*A61B 18/14* (2006.01)
*A61B 18/00* (2006.01)

(52) U.S. Cl.
CPC ........ *A61B 18/082* (2013.01); *A61B 18/1492* (2013.01); *A61B 2018/00267* (2013.01); *A61B 2018/00541* (2013.01)

(58) Field of Classification Search
CPC .............. A61B 18/082; A61B 18/1492; A61B 2018/00267; A61B 2018/00541;
(Continued)

(56) References Cited

U.S. PATENT DOCUMENTS 612,724 A 10/1898 Jonathan
1,155,169 A 9/1915 Starkweather
(Continued)

FOREIGN PATENT DOCUMENTS

CN 1078595 11/1993
DE 19529634 A1 2/1997
(Continued)

OTHER PUBLICATIONS

An S.S., et al., "Airway Smooth Muscle Dynamics: A Common Pathway of Airway Obstruction in Asthma," European Respiratory Journal, 2007, 29 (5), 834-860.
(Continued)

*Primary Examiner* — Michael Peffley
*Assistant Examiner* — Khadijeh Vahdat
(74) *Attorney, Agent, or Firm* — Bookoff McAndrews, PLLC

(57) ABSTRACT

An energy delivery device is disclosed. The energy delivery device may include an elongate member having a proximal end and a distal end, and an energy emitting portion coupled to the distal end of the elongate member. The energy emitting portion may be configured to transition between a first, collapsed configuration and a second, expanded configuration. In addition, the energy emitting portion may include a plurality of legs forming a basket, such that when the energy emitting portion is in the second, expanded configuration a central portion of at least one of the legs includes a substantially straight configuration.

17 Claims, 3 Drawing Sheets

(58) Field of Classification Search
CPC ......... A61B 18/08; A61B 18/10; A61B 18/14; A61B 18/1442; A61B 18/1445; A61B 18/1448
USPC .................................................. 606/41–50
See application file for complete search history.

(56) References Cited

U.S. PATENT DOCUMENTS

| | | |
|---|---|---|
| 1,207,479 A | 12/1916 | Bisgaard |
| 1,216,183 A | 2/1917 | Swingle |
| 2,072,346 A | 3/1937 | Smith |
| 3,320,957 A | 5/1967 | Sokolik |
| 3,568,659 A | 3/1971 | Karnegis |
| 3,667,476 A | 6/1972 | Muller |
| 3,692,029 A | 9/1972 | Adair |
| 3,995,617 A | 12/1976 | Watkins et al. |
| 4,095,602 A | 6/1978 | Leveen |
| 4,116,589 A | 9/1978 | Rishton |
| 4,129,129 A | 12/1978 | Amrine |
| 4,154,246 A | 5/1979 | LeVeen |
| 4,461,283 A | 7/1984 | Doi |
| 4,502,490 A | 3/1985 | Evans et al. |
| 4,503,855 A | 3/1985 | Maslanka |
| 4,512,762 A | 4/1985 | Spears |
| 4,522,212 A | 6/1985 | Gelinas et al. |
| 4,557,272 A | 12/1985 | Carr |
| 4,565,200 A | 1/1986 | Cosman |
| 4,567,882 A | 2/1986 | Heller |
| 4,584,998 A | 4/1986 | McGrail |
| 4,612,934 A | 9/1986 | Borkan |
| 4,621,642 A | 11/1986 | Chen |
| 4,621,882 A | 11/1986 | Krumme |
| 4,625,712 A | 12/1986 | Wampler |
| 4,643,186 A | 2/1987 | Rosen et al. |
| 4,646,737 A | 3/1987 | Hussein et al. |
| 4,674,497 A | 6/1987 | Ogasawara |
| 4,683,890 A | 8/1987 | Hewson |
| 4,704,121 A | 11/1987 | Moise |
| 4,706,688 A | 11/1987 | Don Michael et al. |
| 4,709,698 A | 12/1987 | Johnston et al. |
| 4,739,759 A | 4/1988 | Rexroth et al. |
| 4,754,065 A | 6/1988 | Levenson et al. |
| 4,754,752 A | 7/1988 | Ginsburg et al. |
| 4,765,959 A | 8/1988 | Fukasawa |
| 4,772,112 A | 9/1988 | Zider et al. |
| 4,773,899 A | 9/1988 | Spears |
| 4,779,614 A | 10/1988 | Moise |
| 4,784,135 A | 11/1988 | Blum et al. |
| 4,790,305 A | 12/1988 | Zoltan et al. |
| 4,799,479 A | 1/1989 | Spears |
| 4,802,492 A | 2/1989 | Grunstein |
| 4,817,586 A | 4/1989 | Wampler |
| 4,825,871 A | 5/1989 | Cansell |
| 4,827,935 A | 5/1989 | Geddes et al. |
| 4,846,152 A | 7/1989 | Wampler et al. |
| 4,862,886 A | 9/1989 | Clarke et al. |
| 4,895,557 A | 1/1990 | Moise et al. |
| 4,906,229 A | 3/1990 | Wampler |
| 4,907,589 A | 3/1990 | Cosman |
| 4,908,012 A | 3/1990 | Moise et al. |
| 4,920,978 A | 5/1990 | Colvin |
| 4,944,722 A | 7/1990 | Carriker et al. |
| 4,955,377 A | 9/1990 | Lennox et al. |
| 4,967,765 A | 11/1990 | Turner et al. |
| 4,969,865 A | 11/1990 | Hwang et al. |
| 4,976,709 A | 12/1990 | Sand |
| 4,985,014 A | 1/1991 | Orejola |
| 4,991,603 A | 2/1991 | Cohen et al. |
| 5,009,636 A | 4/1991 | Wortley et al. |
| 5,009,936 A | 4/1991 | Yamanaka et al. |
| 5,010,892 A | 4/1991 | Colvin et al. |
| 5,019,075 A | 5/1991 | Spears et al. |
| 5,027,829 A | 7/1991 | Larsen |
| 5,030,645 A | 7/1991 | Kollonitsch |
| 5,036,848 A | 8/1991 | Hewson |
| 5,053,033 A | 10/1991 | Clarke |
| 5,056,519 A | 10/1991 | Vince |
| 5,074,860 A | 12/1991 | Gregory et al. |
| 5,078,716 A | 1/1992 | Doll |
| 5,084,044 A | 1/1992 | Quint |
| 5,096,916 A | 3/1992 | Skupin |
| 5,100,388 A | 3/1992 | Behl et al. |
| 5,100,423 A | 3/1992 | Fearnot |
| 5,103,804 A | 4/1992 | Abele et al. |
| 5,105,826 A | 4/1992 | Smits et al. |
| 5,106,360 A | 4/1992 | Ishiwara et al. |
| 5,107,830 A | 4/1992 | Younes |
| 5,114,423 A | 5/1992 | Kasprzyk et al. |
| 5,116,864 A | 5/1992 | March et al. |
| 5,117,828 A | 6/1992 | Metzger et al. |
| 5,135,517 A | 8/1992 | McCoy |
| 5,152,286 A | 10/1992 | Sitko et al. |
| 5,165,420 A | 11/1992 | Strickland |
| 5,167,223 A | 12/1992 | Koros et al. |
| 5,170,803 A | 12/1992 | Hewson et al. |
| 5,174,288 A | 12/1992 | Bardy et al. |
| 5,188,602 A | 2/1993 | Nichols |
| 5,191,883 A | 3/1993 | Lennox et al. |
| 5,213,576 A | 5/1993 | Abiuso et al. |
| 5,215,103 A | 6/1993 | Desai |
| 5,231,996 A | 8/1993 | Bardy et al. |
| 5,232,444 A | 8/1993 | Just et al. |
| 5,234,456 A | 8/1993 | Silvestrini |
| 5,254,088 A | 10/1993 | Lundquist et al. |
| 5,255,678 A | 10/1993 | Deslauriers et al. |
| 5,255,679 A | 10/1993 | Imran |
| 5,265,604 A | 11/1993 | Vince |
| 5,269,758 A | 12/1993 | Taheri |
| 5,281,218 A | 1/1994 | Imran |
| 5,292,331 A | 3/1994 | Boneau |
| 5,293,869 A | 3/1994 | Edwards et al. |
| 5,309,910 A | 5/1994 | Edwards et al. |
| 5,311,866 A | 5/1994 | Kagan et al. |
| 5,313,943 A | 5/1994 | Houser et al. |
| 5,324,284 A | 6/1994 | Imran |
| 5,343,936 A | 9/1994 | Beatenbough et al. |
| 5,345,936 A | 9/1994 | Pomeranz et al. |
| 5,366,443 A | 11/1994 | Eggers et al. |
| 5,368,591 A | 11/1994 | Lennox et al. |
| 5,370,644 A | 12/1994 | Langberg |
| 5,370,679 A | 12/1994 | Atlee, III |
| 5,374,287 A | 12/1994 | Rubin |
| 5,383,917 A | 1/1995 | Desai et al. |
| 5,393,207 A | 2/1995 | Maher et al. |
| 5,394,880 A | 3/1995 | Atlee, III |
| 5,396,887 A | 3/1995 | Imran |
| 5,400,778 A | 3/1995 | Jonson et al. |
| 5,400,783 A | 3/1995 | Pomeranz et al. |
| 5,411,025 A | 5/1995 | Webster |
| 5,415,166 A | 5/1995 | Imran |
| 5,415,656 A | 5/1995 | Tihon et al. |
| 5,417,687 A | 5/1995 | Nardella et al. |
| 5,422,362 A | 6/1995 | Vincent et al. |
| 5,423,744 A | 6/1995 | Gencheff et al. |
| 5,423,811 A | 6/1995 | Imran et al. |
| 5,425,023 A | 6/1995 | Haraguchi et al. |
| 5,425,703 A | 6/1995 | Feiring |
| 5,425,811 A | 6/1995 | Mashita |
| 5,431,696 A | 7/1995 | Atlee, III |
| 5,433,730 A | 7/1995 | Alt |
| 5,437,665 A | 8/1995 | Munro |
| 5,443,470 A | 8/1995 | Stern et al. |
| 5,454,782 A | 10/1995 | Perkins |
| 5,456,667 A | 10/1995 | Ham et al. |
| 5,458,596 A | 10/1995 | Lax et al. |
| 5,465,717 A | 11/1995 | Imran et al. |
| 5,471,982 A | 12/1995 | Edwards et al. |
| 5,474,530 A | 12/1995 | Passafaro et al. |
| 5,478,309 A | 12/1995 | Sweezer et al. |
| 5,496,271 A | 3/1996 | Burton et al. |
| 5,496,311 A | 3/1996 | Abele et al. |
| 5,496,312 A | 3/1996 | Klicek |
| 5,500,011 A | 3/1996 | Desai |
| 5,505,728 A | 4/1996 | Ellman et al. |

(56) References Cited

U.S. PATENT DOCUMENTS

| | | |
|---|---|---|
| 5,505,730 A | 4/1996 | Edwards |
| 5,507,791 A | 4/1996 | Sit'ko |
| 5,509,419 A | 4/1996 | Edwards et al. |
| 5,522,862 A | 6/1996 | Testerman et al. |
| 5,531,779 A | 7/1996 | Dahl et al. |
| 5,540,681 A | 7/1996 | Strul et al. |
| 5,545,161 A | 8/1996 | Imran |
| 5,545,193 A | 8/1996 | Fleischman et al. |
| 5,547,469 A | 8/1996 | Rowland et al. |
| 5,549,559 A | 8/1996 | Eshel |
| 5,549,655 A | 8/1996 | Erickson |
| 5,549,661 A | 8/1996 | Kordis et al. |
| RE35,330 E | 9/1996 | Malone et al. |
| 5,558,073 A | 9/1996 | Pomeranz et al. |
| 5,562,608 A | 10/1996 | Sekins et al. |
| 5,571,074 A | 11/1996 | Buckman et al. |
| 5,571,088 A | 11/1996 | Lennox et al. |
| 5,574,059 A | 11/1996 | Regunathan et al. |
| 5,575,810 A | 11/1996 | Swanson et al. |
| 5,578,072 A | 11/1996 | Barone et al. |
| 5,582,609 A | 12/1996 | Swanson et al. |
| 5,588,432 A | 12/1996 | Crowley |
| 5,588,812 A | 12/1996 | Taylor et al. |
| 5,595,183 A | 1/1997 | Swanson et al. |
| 5,598,848 A | 2/1997 | Swanson et al. |
| 5,599,345 A | 2/1997 | Edwards et al. |
| 5,601,088 A | 2/1997 | Swanson et al. |
| 5,605,157 A | 2/1997 | Panescu et al. |
| 5,607,419 A | 3/1997 | Amplatz et al. |
| 5,607,462 A | 3/1997 | Imran |
| 5,620,438 A | 4/1997 | Amplatz et al. |
| 5,623,940 A | 4/1997 | Daikuzono |
| 5,624,439 A | 4/1997 | Edwards et al. |
| 5,626,618 A | 5/1997 | Ward et al. |
| 5,630,425 A | 5/1997 | Panescu et al. |
| 5,630,794 A | 5/1997 | Lax et al. |
| 5,634,471 A | 6/1997 | Fairfax et al. |
| 5,641,326 A | 6/1997 | Adams |
| 5,647,870 A | 7/1997 | Kordis et al. |
| 5,660,175 A | 8/1997 | Dayal |
| 5,678,535 A | 10/1997 | DiMarco |
| 5,680,860 A | 10/1997 | Imran |
| 5,681,280 A | 10/1997 | Rusk et al. |
| 5,681,308 A | 10/1997 | Edwards et al. |
| 5,687,723 A | 11/1997 | Avitall |
| 5,688,267 A | 11/1997 | Panescu et al. |
| 5,693,078 A | 12/1997 | Desai et al. |
| 5,694,934 A | 12/1997 | Edelman |
| 5,695,471 A | 12/1997 | Wampler |
| 5,699,799 A | 12/1997 | Xu et al. |
| 5,702,386 A | 12/1997 | Stern et al. |
| 5,707,218 A | 1/1998 | Maher et al. |
| 5,707,336 A | 1/1998 | Rubin |
| 5,707,352 A | 1/1998 | Sekins et al. |
| 5,722,401 A | 3/1998 | Pietroski et al. |
| 5,722,403 A | 3/1998 | McGee et al. |
| 5,722,416 A | 3/1998 | Swanson et al. |
| 5,725,525 A | 3/1998 | Kordis |
| 5,727,569 A | 3/1998 | Benetti et al. |
| 5,728,094 A | 3/1998 | Edwards |
| 5,730,128 A | 3/1998 | Pomeranz et al. |
| 5,730,704 A | 3/1998 | Avitall |
| 5,730,726 A | 3/1998 | Klingenstein |
| 5,730,741 A | 3/1998 | Horzewski et al. |
| 5,735,846 A | 4/1998 | Panescu et al. |
| 5,740,808 A | 4/1998 | Panescu et al. |
| 5,741,248 A | 4/1998 | Stern et al. |
| 5,752,518 A | 5/1998 | McGee et al. |
| 5,755,714 A | 5/1998 | Murphy-Chutorian |
| 5,755,715 A | 5/1998 | Stern et al. |
| 5,755,753 A | 5/1998 | Knowlton |
| 5,759,158 A | 6/1998 | Swanson |
| 5,765,568 A | 6/1998 | Sweezer et al. |
| 5,769,846 A | 6/1998 | Edwards et al. |
| 5,772,590 A | 6/1998 | Webster |
| 5,779,669 A | 7/1998 | Haissaguerre et al. |
| 5,779,698 A | 7/1998 | Clayman et al. |
| 5,782,239 A | 7/1998 | Webster |
| 5,782,797 A | 7/1998 | Schweich et al. |
| 5,782,827 A | 7/1998 | Gough et al. |
| 5,782,848 A | 7/1998 | Lennox |
| 5,782,899 A | 7/1998 | Imran |
| 5,792,064 A | 8/1998 | Panescu et al. |
| 5,795,303 A | 8/1998 | Swanson et al. |
| 5,800,375 A | 9/1998 | Sweezer et al. |
| 5,807,306 A | 9/1998 | Shapland et al. |
| 5,810,757 A | 9/1998 | Sweezer et al. |
| 5,810,807 A | 9/1998 | Ganz et al. |
| 5,817,028 A | 10/1998 | Anderson |
| 5,817,073 A | 10/1998 | Krespi |
| 5,820,554 A | 10/1998 | Davis et al. |
| 5,823,189 A | 10/1998 | Kordis |
| 5,827,277 A | 10/1998 | Edwards |
| 5,833,651 A | 11/1998 | Donovan et al. |
| 5,836,905 A | 11/1998 | Lemelson et al. |
| 5,836,947 A | 11/1998 | Fleischman et al. |
| 5,837,001 A | 11/1998 | Mackey |
| 5,843,075 A | 12/1998 | Taylor |
| 5,843,077 A | 12/1998 | Edwards |
| 5,846,238 A | 12/1998 | Jackson et al. |
| 5,848,969 A | 12/1998 | Panescu et al. |
| 5,848,972 A | 12/1998 | Triedman et al. |
| 5,849,026 A | 12/1998 | Zhou et al. |
| 5,855,577 A | 1/1999 | Murphy-Chutorian et al. |
| 5,860,974 A | 1/1999 | Abele |
| 5,863,291 A | 1/1999 | Schaer |
| 5,865,791 A | 2/1999 | Whayne et al. |
| 5,868,740 A | 2/1999 | LeVeen et al. |
| 5,871,443 A | 2/1999 | Edwards et al. |
| 5,871,523 A | 2/1999 | Fleischman et al. |
| 5,873,852 A | 2/1999 | Vigil et al. |
| 5,873,865 A | 2/1999 | Horzewski et al. |
| 5,876,340 A | 3/1999 | Tu et al. |
| 5,876,399 A | 3/1999 | Chia et al. |
| 5,881,727 A | 3/1999 | Edwards |
| 5,882,346 A | 3/1999 | Pomeranz et al. |
| 5,891,135 A | 4/1999 | Jackson et al. |
| 5,891,136 A | 4/1999 | McGee et al. |
| 5,891,138 A | 4/1999 | Tu et al. |
| 5,893,847 A | 4/1999 | Kordis |
| 5,897,554 A | 4/1999 | Chia et al. |
| 5,899,882 A | 5/1999 | Waksman et al. |
| 5,904,651 A | 5/1999 | Swanson et al. |
| 5,904,711 A | 5/1999 | Flom et al. |
| 5,906,636 A | 5/1999 | Casscells, III et al. |
| 5,908,445 A | 6/1999 | Whayne et al. |
| 5,908,446 A | 6/1999 | Imran |
| 5,908,839 A | 6/1999 | Levitt et al. |
| 5,911,218 A | 6/1999 | DiMarco |
| 5,916,235 A | 6/1999 | Guglielmi |
| 5,919,147 A | 7/1999 | Jain |
| 5,919,172 A | 7/1999 | Golba |
| 5,924,424 A | 7/1999 | Stevens et al. |
| 5,928,228 A | 7/1999 | Kordis et al. |
| 5,931,835 A | 8/1999 | Mackey |
| 5,935,079 A | 8/1999 | Swanson et al. |
| 5,941,869 A | 8/1999 | Patterson et al. |
| 5,951,494 A | 9/1999 | Wang et al. |
| 5,951,546 A | 9/1999 | Lorentzen |
| 5,954,661 A | 9/1999 | Greenspon et al. |
| 5,954,662 A | 9/1999 | Swanson et al. |
| 5,954,717 A | 9/1999 | Behl et al. |
| 5,957,961 A | 9/1999 | Maguire et al. |
| 5,964,753 A | 10/1999 | Edwards |
| 5,964,796 A | 10/1999 | Imran |
| 5,971,983 A | 10/1999 | Lesh |
| 5,972,026 A | 10/1999 | Laufer et al. |
| 5,976,175 A | 11/1999 | Hirano et al. |
| 5,976,709 A | 11/1999 | Kageyama et al. |
| 5,979,456 A | 11/1999 | Magovern |
| 5,980,563 A | 11/1999 | Tu et al. |
| 5,984,917 A | 11/1999 | Fleischman et al. |
| 5,984,971 A | 11/1999 | Faccioli et al. |
| 5,991,650 A | 11/1999 | Swanson et al. |

(56) References Cited

U.S. PATENT DOCUMENTS

| | | |
|---|---|---|
| 5,992,419 A | 11/1999 | Sterzer et al. |
| 5,993,462 A | 11/1999 | Pomeranz et al. |
| 5,997,534 A | 12/1999 | Tu et al. |
| 5,999,855 A | 12/1999 | DiMarco |
| 6,001,054 A | 12/1999 | Regulla et al. |
| 6,003,517 A | 12/1999 | Sheffield et al. |
| 6,004,269 A | 12/1999 | Crowley et al. |
| 6,006,755 A | 12/1999 | Edwards |
| 6,008,211 A | 12/1999 | Robinson et al. |
| 6,009,877 A | 1/2000 | Edwards |
| 6,010,500 A | 1/2000 | Sherman et al. |
| 6,014,579 A | 1/2000 | Pomeranz et al. |
| 6,016,437 A | 1/2000 | Tu et al. |
| 6,023,638 A | 2/2000 | Swanson |
| 6,024,740 A | 2/2000 | Lesh et al. |
| 6,029,091 A | 2/2000 | de la Rama et al. |
| 6,033,397 A | 3/2000 | Laufer et al. |
| 6,036,687 A | 3/2000 | Laufer et al. |
| 6,036,689 A | 3/2000 | Tu et al. |
| 6,039,731 A | 3/2000 | Taylor et al. |
| 6,042,580 A | 3/2000 | Simpson |
| 6,045,549 A | 4/2000 | Smethers et al. |
| 6,045,550 A | 4/2000 | Simpson et al. |
| 6,050,992 A | 4/2000 | Nichols |
| 6,053,172 A | 4/2000 | Hovda et al. |
| 6,053,909 A | 4/2000 | Shadduck |
| 6,056,744 A | 5/2000 | Edwards |
| 6,056,769 A | 5/2000 | Epstein et al. |
| 6,063,078 A | 5/2000 | Wittkampf |
| 6,071,280 A | 6/2000 | Edwards et al. |
| 6,071,281 A | 6/2000 | Burnside et al. |
| 6,071,282 A | 6/2000 | Fleischman |
| 6,083,255 A | 7/2000 | Laufer et al. |
| 6,090,104 A | 7/2000 | Webster |
| 6,092,528 A | 7/2000 | Edwards |
| 6,102,886 A | 8/2000 | Lundquist et al. |
| 6,106,522 A | 8/2000 | Fleischman et al. |
| 6,106,524 A | 8/2000 | Eggers et al. |
| 6,123,702 A | 9/2000 | Swanson et al. |
| 6,123,703 A | 9/2000 | Tu et al. |
| 6,129,725 A | 10/2000 | Tu et al. |
| 6,139,527 A | 10/2000 | Laufer et al. |
| 6,139,571 A | 10/2000 | Fuller et al. |
| 6,142,993 A | 11/2000 | Whayne et al. |
| 6,143,013 A | 11/2000 | Samson et al. |
| 6,149,647 A | 11/2000 | Tu et al. |
| 6,152,143 A | 11/2000 | Edwards |
| 6,152,899 A | 11/2000 | Farley et al. |
| 6,159,194 A | 12/2000 | Eggers et al. |
| 6,179,833 B1 | 1/2001 | Taylor |
| 6,183,468 B1 | 2/2001 | Swanson et al. |
| 6,198,970 B1 | 3/2001 | Freed et al. |
| 6,200,311 B1 | 3/2001 | Danek et al. |
| 6,200,332 B1 | 3/2001 | Del Giglio |
| 6,200,333 B1 | 3/2001 | Laufer |
| 6,210,367 B1 | 4/2001 | Carr |
| 6,212,433 B1 | 4/2001 | Behl |
| 6,214,002 B1 | 4/2001 | Fleischman et al. |
| 6,216,043 B1 | 4/2001 | Swanson et al. |
| 6,216,044 B1 | 4/2001 | Kordis |
| 6,217,576 B1 | 4/2001 | Tu et al. |
| 6,235,024 B1 | 5/2001 | Tu |
| 6,241,727 B1 | 6/2001 | Tu et al. |
| 6,245,065 B1 | 6/2001 | Panescu et al. |
| 6,254,598 B1 | 7/2001 | Edwards et al. |
| 6,258,087 B1 | 7/2001 | Edwards et al. |
| 6,264,653 B1 | 7/2001 | Falwell |
| 6,269,813 B1 | 8/2001 | Fitzgerald et al. |
| 6,270,476 B1 | 8/2001 | Santoianni et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,287,304 B1 | 9/2001 | Eggers et al. |
| 6,296,639 B1 | 10/2001 | Truckai et al. |
| 6,319,251 B1 | 11/2001 | Tu et al. |
| 6,322,559 B1 | 11/2001 | Daulton et al. |
| 6,322,584 B2 | 11/2001 | Ingle et al. |
| 6,338,727 B1 | 1/2002 | Noda et al. |
| 6,338,836 B1 | 1/2002 | Kuth et al. |
| 6,346,104 B2 | 2/2002 | Daly et al. |
| 6,355,031 B1 | 3/2002 | Edwards et al. |
| 6,379,352 B1 | 4/2002 | Reynolds et al. |
| 6,409,723 B1 | 6/2002 | Edwards |
| 6,411,852 B1 | 6/2002 | Danek et al. |
| 6,416,511 B1 | 7/2002 | Lesh et al. |
| 6,416,740 B1 | 7/2002 | Unger |
| 6,423,105 B1 | 7/2002 | Iijima et al. |
| 6,425,895 B1 | 7/2002 | Swanson et al. |
| 6,440,129 B1 | 8/2002 | Simpson |
| 6,442,435 B2 | 8/2002 | King et al. |
| 6,458,121 B1 | 10/2002 | Rosenstock et al. |
| 6,460,545 B2 | 10/2002 | Kordis |
| 6,488,673 B1 | 12/2002 | Laufer et al. |
| 6,488,679 B1 | 12/2002 | Swanson et al. |
| 6,493,589 B1 | 12/2002 | Medhkour et al. |
| 6,494,880 B1 | 12/2002 | Swanson et al. |
| 6,496,738 B2 | 12/2002 | Carr |
| 6,514,246 B1 | 2/2003 | Swanson et al. |
| 6,514,247 B1 | 2/2003 | McGaffigan et al. |
| 6,526,320 B2 | 2/2003 | Mitchell |
| 6,529,756 B1 | 3/2003 | Phan et al. |
| 6,544,226 B1 | 4/2003 | Gaiser et al. |
| 6,544,262 B2 | 4/2003 | Fleischman |
| 6,547,788 B1 | 4/2003 | Maguire et al. |
| 6,558,378 B2 | 5/2003 | Sherman et al. |
| 6,572,612 B2 | 6/2003 | Stewart et al. |
| 6,575,623 B2 | 6/2003 | Werneth |
| 6,575,969 B1 | 6/2003 | Rittman, III et al. |
| 6,582,427 B1 | 6/2003 | Goble et al. |
| 6,582,430 B2 | 6/2003 | Hall |
| 6,589,235 B2 | 7/2003 | Wong et al. |
| 6,610,054 B1 | 8/2003 | Edwards et al. |
| 6,620,159 B2 | 9/2003 | Hegde |
| 6,626,903 B2 | 9/2003 | McGuckin et al. |
| 6,634,363 B1 | 10/2003 | Danek et al. |
| 6,635,056 B2 | 10/2003 | Kadhiresan et al. |
| 6,638,273 B1 | 10/2003 | Farley et al. |
| 6,640,120 B1 | 10/2003 | Swanson et al. |
| 6,645,200 B1 | 11/2003 | Koblish et al. |
| 6,652,548 B2 | 11/2003 | Evans et al. |
| 6,669,693 B2 | 12/2003 | Friedman |
| 6,673,068 B1 | 1/2004 | Berube |
| 6,692,492 B2 | 2/2004 | Simpson et al. |
| 6,699,243 B2 | 3/2004 | West et al. |
| 6,714,822 B2 | 3/2004 | King et al. |
| 6,723,091 B2 | 4/2004 | Goble et al. |
| 6,743,197 B1 | 6/2004 | Edwards |
| 6,749,604 B1 | 6/2004 | Eggers et al. |
| 6,749,606 B2 | 6/2004 | Keast et al. |
| 6,767,347 B2 | 7/2004 | Sharkey et al. |
| 6,770,070 B1 | 8/2004 | Balbierz |
| 6,802,843 B2 | 10/2004 | Truckai et al. |
| 6,805,131 B2 | 10/2004 | Kordis |
| 6,837,888 B2 | 1/2005 | Ciarrocca et al. |
| 6,840,243 B2 | 1/2005 | Deem et al. |
| 6,849,073 B2 | 2/2005 | Hoey et al. |
| 6,852,091 B2 | 2/2005 | Edwards et al. |
| 6,852,110 B2 | 2/2005 | Roy et al. |
| 6,866,662 B2 | 3/2005 | Fuimaono et al. |
| 6,881,213 B2 | 4/2005 | Ryan et al. |
| 6,893,436 B2 | 5/2005 | Woodard et al. |
| 6,893,439 B2 | 5/2005 | Fleischman |
| 6,895,267 B2 | 5/2005 | Panescu et al. |
| 6,904,303 B2 | 6/2005 | Phan et al. |
| 6,917,834 B2 | 7/2005 | Koblish et al. |
| 6,939,346 B2 | 9/2005 | Kannenberg et al. |
| 6,954,977 B2 | 10/2005 | Maguire et al. |
| 7,027,869 B2 | 4/2006 | Danek et al. |
| 7,043,307 B1 | 5/2006 | Zelickson et al. |
| 7,104,987 B2 | 9/2006 | Biggs et al. |
| 7,104,990 B2 | 9/2006 | Jenkins et al. |
| 7,118,568 B2 | 10/2006 | Hassett et al. |
| 7,122,033 B2 | 10/2006 | Wood |
| 7,131,445 B2 | 11/2006 | Amoah |

(56) References Cited

U.S. PATENT DOCUMENTS

| | | |
|---|---|---|
| 7,186,251 B2 | 3/2007 | Malecki et al. |
| 7,198,635 B2 | 4/2007 | Danek et al. |
| 7,200,445 B1 | 4/2007 | Dalbec et al. |
| 7,241,295 B2 | 7/2007 | Maguire |
| 7,255,693 B1 | 8/2007 | Johnston et al. |
| 7,264,002 B2 | 9/2007 | Danek et al. |
| 7,266,414 B2 | 9/2007 | Cornelius et al. |
| 7,273,055 B2 | 9/2007 | Danek et al. |
| 7,425,212 B1 | 9/2008 | Danek et al. |
| 7,542,802 B2 | 6/2009 | Biggs et al. |
| 7,556,624 B2 | 7/2009 | Laufer et al. |
| 7,740,017 B2 | 6/2010 | Danek et al. |
| 7,949,407 B2 * | 5/2011 | Kaplan et al. ................ 607/101 |
| 8,161,978 B2 | 4/2012 | Danek et al. |
| 8,465,486 B2 | 6/2013 | Danek et al. |
| 8,584,681 B2 | 11/2013 | Danek et al. |
| 2003/0050631 A1 | 3/2003 | Mody et al. |
| 2003/0065371 A1 | 4/2003 | Satake |
| 2003/0069570 A1 | 4/2003 | Witzel et al. |
| 2003/0187430 A1 | 10/2003 | Vorisek |
| 2003/0236455 A1 | 12/2003 | Swanson et al. |
| 2004/0153056 A1 | 8/2004 | Muller et al. |
| 2004/0249401 A1 | 12/2004 | Rabiner et al. |
| 2005/0010270 A1 | 1/2005 | Laufer |
| 2005/0096644 A1 | 5/2005 | Hall et al. |
| 2005/0096647 A1* | 5/2005 | Steinke ............. A61B 18/1492 606/41 |
| 2005/0171396 A1 | 8/2005 | Pankratov et al. |
| 2005/0193279 A1 | 9/2005 | Daners |
| 2005/0203503 A1 | 9/2005 | Edwards et al. |
| 2005/0240176 A1 | 10/2005 | Oral et al. |
| 2005/0251128 A1 | 11/2005 | Amoah |
| 2006/0062808 A1 | 3/2006 | Laufer et al. |
| 2006/0079887 A1 | 4/2006 | Buysse et al. |
| 2006/0089637 A1 | 4/2006 | Werneth et al. |
| 2006/0135953 A1 | 6/2006 | Kania et al. |
| 2006/0137698 A1 | 6/2006 | Danek et al. |
| 2006/0247617 A1 | 11/2006 | Danek et al. |
| 2006/0247618 A1 | 11/2006 | Kaplan et al. |
| 2006/0247619 A1 | 11/2006 | Kaplan et al. |
| 2006/0247726 A1 | 11/2006 | Biggs et al. |
| 2006/0247727 A1 | 11/2006 | Biggs et al. |
| 2006/0247746 A1 | 11/2006 | Danek et al. |
| 2006/0254600 A1 | 11/2006 | Danek et al. |
| 2006/0278243 A1 | 12/2006 | Danek et al. |
| 2006/0278244 A1 | 12/2006 | Danek et al. |
| 2006/0282071 A1 | 12/2006 | Utley et al. |
| 2007/0074719 A1 | 4/2007 | Danek et al. |
| 2007/0083194 A1 | 4/2007 | Kunis et al. |
| 2007/0083197 A1 | 4/2007 | Danek et al. |
| 2007/0102011 A1 | 5/2007 | Danek et al. |
| 2007/0106292 A1 | 5/2007 | Kaplan et al. |
| 2007/0106296 A1 | 5/2007 | Laufer et al. |
| 2007/0106348 A1 | 5/2007 | Laufer |
| 2007/0118184 A1 | 5/2007 | Danek et al. |
| 2007/0118190 A1 | 5/2007 | Danek et al. |
| 2007/0123958 A1 | 5/2007 | Laufer |
| 2007/0123961 A1 | 5/2007 | Danek et al. |
| 2007/0129720 A1 | 6/2007 | Demarais et al. |
| 2008/0004596 A1 | 1/2008 | Yun et al. |
| 2008/0097424 A1 | 4/2008 | Wizeman et al. |
| 2008/0255642 A1 | 10/2008 | Zarins et al. |
| 2009/0018538 A1 | 1/2009 | Webster et al. |
| 2009/0030477 A1 | 1/2009 | Jarrard |
| 2009/0043301 A1 | 2/2009 | Jarrard et al. |
| 2009/0069797 A1 | 3/2009 | Danek et al. |
| 2009/0112203 A1 | 4/2009 | Danek et al. |
| 2009/0143705 A1 | 6/2009 | Danek et al. |
| 2009/0143776 A1 | 6/2009 | Danek et al. |
| 2009/0192505 A1 | 7/2009 | Askew et al. |
| 2009/0192508 A1 | 7/2009 | Laufer et al. |
| 2009/0306644 A1 | 12/2009 | Mayse et al. |
| 2010/0160906 A1 | 6/2010 | Jarrard |
| 2011/0118726 A1 | 5/2011 | De La Rama et al. |

FOREIGN PATENT DOCUMENTS

| | | |
|---|---|---|
| EP | 189329 A3 | 6/1987 |
| EP | 286145 A2 | 10/1988 |
| EP | 286145 A3 | 10/1990 |
| EP | 282225 B1 | 6/1992 |
| EP | 280225 A2 | 8/1998 |
| EP | 0873710 A2 | 10/1998 |
| EP | 908713 A1 | 4/1999 |
| EP | 908150 B1 | 5/2003 |
| EP | 768091 B1 | 7/2003 |
| EP | 1297795 B1 | 8/2005 |
| EP | 2170459 B1 | 2/2014 |
| FR | 2659240 B1 | 7/1997 |
| GB | 2233293 A | 1/1991 |
| GB | 2233293 B | 2/1994 |
| JP | 59167707 A2 | 9/1984 |
| JP | 7289557 A | 11/1995 |
| JP | 9047518 A2 | 2/1997 |
| JP | 9243837 A2 | 9/1997 |
| JP | 10026709 A2 | 1/1998 |
| RU | 2053814 C1 | 2/1996 |
| RU | 2091054 C1 | 9/1997 |
| SU | 545358 T | 2/1977 |
| WO | WO-8911311 A1 | 11/1989 |
| WO | WO-9304734 A1 | 3/1993 |
| WO | WO-9502370 A3 | 3/1995 |
| WO | WO-9510322 A1 | 4/1995 |
| WO | WO-9604860 A1 | 2/1996 |
| WO | WO-9610961 A1 | 4/1996 |
| WO | WO-9732532 A1 | 9/1997 |
| WO | WO-9733715 A1 | 9/1997 |
| WO | WO-9737715 A1 | 10/1997 |
| WO | WO-9740751 A1 | 11/1997 |
| WO | WO-9844854 A1 | 10/1998 |
| WO | WO-9852480 A1 | 11/1998 |
| WO | WO-9856234 A1 | 12/1998 |
| WO | WO-9856324 A1 | 12/1998 |
| WO | WO-9903413 A1 | 1/1999 |
| WO | WO-9858681 A3 | 3/1999 |
| WO | WO-9913779 A2 | 3/1999 |
| WO | WO-9932040 A1 | 7/1999 |
| WO | WO-9934741 A1 | 7/1999 |
| WO | WO-9944506 A1 | 9/1999 |
| WO | WO-9945855 A1 | 9/1999 |
| WO | WO-9964109 A1 | 12/1999 |
| WO | WO-0051510 A1 | 9/2000 |
| WO | WO-0062699 A3 | 10/2000 |
| WO | WO-0103642 A1 | 1/2001 |
| WO | WO-0232333 A1 | 4/2002 |
| WO | WO-0232334 A1 | 4/2002 |
| WO | WO-2006007284 A2 | 1/2006 |
| WO | WO-2006044581 A2 | 4/2006 |
| WO | WO-2008051706 A2 | 5/2008 |
| WO | WO-2009082433 A2 | 7/2009 |
| WO | WO-2009137819 A1 | 11/2009 |

OTHER PUBLICATIONS

Brown R.H., et al., "Effect of Bronchial Thermoplasty on Airway Distensibility," European Respiratory Journal, 2005, 26 (2), 277-282.

Chhajed P.N., et al., "Will there be a Role for Bronchoscopic Radiofrequency Ablation", Journal of Bronchology, 2005, 12 (3), 184-186.

Cox G., et al., "Asthma Control during the Year after Bronchial Thermoplasty," New England journal of medicine, 2007, 356 (13), 1327-1337.

Cox G., et al., "Bronchial Thermoplasty for Asthma," American Journal of Respiratory and Critical Care Medicine, 2006, 173 (9), 965-969.

Cox G., et al., "Impact of Bronchial Thermoplasty on Asthma Status: Interim Results from the Air Trial," 2006, 1 page.

Cox G., et al., "Radiofrequency Ablation of Airways Smooth Muscle for Sustained Treatment of Asthma: Preliminary Investigations," European Respiratory Journal, 2004, 24 (4), 659-663.

(56) References Cited

OTHER PUBLICATIONS

Danek C.J., et al., "Reduction in Airway Hyperresponsiveness to Methacholine by the Application of RF Energy in Dogs," Journal of Applied Physiology, 2004, 97 (5), 1946-1953.
International Search Report for Application No. PCT/US00/05412, mailed on Jun. 20, 2000, 2 pages.
International Search Report for Application No. PCT/US00/18197, mailed on Oct. 3, 2000, 1 page.
International Search Report for Application No. PCT/US00/28745, mailed on Mar. 28, 2001, 6 pages.
International Search Report for Application No. PCT/US01/32321, mailed on Jan. 18, 2002, 2 pages.
International Search Report for Application No. PCT/US98/03759, mailed on Jul. 30, 1998, 1 page.
International Search Report for Application No. PCT/US98/26227, mailed on Mar. 25, 1999, 1 page.
International Search Report for Application No. PCT/US99/00232, mailed on Mar. 4, 1999, 1 page.
International Search Report for Application No. PCT/US99/12986, mailed on Sep. 29, 1999, 1 page.
Ivanyuta O.M., et al., "Effect of Low-Power Laser Irradiation of Bronchial Mucosa on the State of Systemic and Local Immunity in Patients with Chronic Bronchitis," Problemy Tuberkuleza, 1991, 6, 26-29.
Johnson S. R., et al., "Synthetic Functions of Airways Smooth Muscle in Asthma," Trends Pharmacol. Sci., 1997, 18 (8), 288-292.
Kitamura S., "Color Atlas of Clinical Application of Fiberoptic Bronchoscopy," 1990, Year Book Medical Publishers, 2 pages.
Lim E.C., et al., "Botulinum Toxin: A Novel Therapeutic Option for Bronchial Asthma", Medical Hypotheses, 2006, 66 (5), 915-919.
Mitzner W., "Airway Smooth Muscle the Appendix of the Lung," American Journal of Respiratory and Critical Care Medicine, 2004, 169 (7), 787-790.
Notice of final Rejection, Japanese Patent Application No. 2000-553172, dated Sep. 2, 2008, 5 pages.
Provotorov V.M., et al., "The Clinical Efficacy of Treating Patients with Nonspecific Lung Diseases Using Low-energy Laser Irradiation and Intrapulmonary Drug Administration," Terapevticheskii Arkhiv, 1991, 62 (12), 18-23.
Solway J., et al., "Airway Smooth Muscle as a Target for Asthma Therapy," New England Journal of medicine, 2007, 356 (13), 1367-1369.
Sterk P.J., et al., "Heterogeneity of Airway Hyperresponsiveness: Time for Unconventional, But Traditional, Studies," Journal of Applied Physiology, 2004, 96 (6), 2017-2018.
Toma T.P., et al., "Brave New World for Interventional Bronchoscopy," Thorax, 2005, 60 (3), 180-181.
Trow T.K., "Clinical Year in Review I: Diagnostic Imaging, Asthma, Lung Transplantation, and Interventional Pulmonology," Proceedings of the American Thoracic Society, 2006, 3 (7), 553-556.
Vorotnev A.I., et al., "The Treatment of Patients with Chronic Obstructive Bronchitis by Using a Low-power Laser at a General Rehabilitation Center," Terapevticheskii Arkhiv, 1997, 69 (3), 17-19.
Wiggs B.R., et al., "On the Mechanism of Mucosal Folding in Normal and Asthmatic Airways," Journal of Applied Physiology, 1997, 83 (6), 1814-1821.
Wilson S.R., et al., "Global Assessment after Bronchial Thermoplasty: The Patients Perspective," Journal of Outcomes Research, 2006, 10, 37-46.
Bel E.H., ""Hot stuff": Bronchial Thermoplasty for Asthma," American Journal of Respiratory and Critical Care Medicine, 2006, 173 (9), 941-943.
Brown R.H., et al., "In Vivo evaluation of the Effectiveness of Bronchial Thermoplasty with Computed Tomography," Journal of Applied Physiology, 2005, 98 (5), 1603-1606.
Abandoned U.S. Appl. No. 09/095,323, filed Jun. 10, 1998, 29 pages.
Abandoned U.S. Appl. No. 09/244,173, filed Feb. 4, 1999, 47 pages.
Cox G., et al., "Asthma Intervention Research (AIR) Trial Evaluating Bronchial Thermoplasty: Early Results," American Thoracic Society Annual Meeting, 2002, 1 page.
Cox G., et al., "Bronchial Thermoplasty: Long-Term Follow-Up and Patient Satisfaction," Chest, 2004, 126 (4), 822s.
Cox G., et al., "Bronchial Thermoplasty: One-Year Update, American Thoracic Society Annual Meeting," American Journal of Respiratory and Critical Care Medicine, 2004, 169, A313.
Cox G., et al., "Clinical Experience with Bronchial Thermoplasty for the Treatment of Asthma," Chest, 2003, 124, 106S.
Cox G., et al., "Development of a Novel Bronchoscopic Therapy for Asthma," Journal of Allergy and Clinical Immunology, 2003, 113 (2), S33.
Cox G., et al., "Early Clinical Experience with Bronchial Thermoplasty for the Treatment of Asthma," American Thoracic Society Annual Meeting, 2002, 1068.
Danek C.J., et al., "Bronchial Thermoplasty Reduces Canine Airway Responsiveness to Local Methacholine Challenge," American Thoracic Society Annual Meeting, 2002, 1 page.
Dierkesmann R., "Indication and Results of Endobronchial Laser Therapy," Lung, 1990, 168, 1095-1102.
Hogg J. C., "The Pathology of Asthma," APMIS, 1997, 105 (10), 735-745.
James A.L., et al., "The Mechanics of Airway Narrowing in Asthma," American Review of Respiratory Diseases, 1989, 139 (1), pp. 242-246.
Laviolette M., et al., "Asthma Intervention Research (Air) Trial: Early Safety Assessment of Bronchial Thermoplasty," American Journal of Respiratory and Critical Care Medicine, 2004, 169, A314.
Leff A., et al., "Bronchial Thermoplasty Alters Airway Smooth Muscle and Reduces Responsiveness in Dogs: A Possible Procedure for the Treatment of Asthma," American Thoracic Society Annual Meeting, 2002, 1 page.
Lombard C.M., et al., "Histologic Effects of Bronchial Thermoplasty of Canine and Human Airways,"American Thoracic Society Annual Meeting, 2002, 1 page.
Macklem P. T., "Mechanical Factors Determining Maximum Bronchoconstriction," European Respiratory Journal, 1989, 6, 516s-519s.
Mayse M.L., et al., "Clinical Pearls for Bronchial Thermoplasty," Journal of Bronchology, 2007, 14 (2), 115-123.
Miller J.D., et al., "A Prospective Feasibility Study of Bronchial Thermoplasty in the Human Airway," Chest, 2005, 127 (6), 1999-2006.
Miller J.D., et al., "Bronchial Thermoplasty is Well Tolerated by Non-Asthmatic Patients Requiring Lobectomy," American Thoracic Society Annual Meeting, 2002, 1 page.
Netter F.H., "Respiratory System: A Compilation of Paintings Depicting Anatomy and Embryology, Physiology, Pathology, Pathophysiology, and Clinical Features and Treatment of Diseases,In the CIBA Collection of Medical Illustrations M.B. Divertie, ed., Summit: New Jerse," 1979, 7, 119-135.
Rubin A., et al., "Bronchial Thermoplasty Improves Asthma Status of Moderate to Severe Perisstent Asthmatics Over and Above Current Standard-of-Care," American College of Chest Physicians, 2006, 2 pages.
Shesterina M.V., et al., "Effect of Laser Therapy on Immunity in Patients with Bronchial Asthma and Pulmonary Tuberculosis," Problemy Tuberkuleza, 1994, 5, 23-26.
Vasilotta P.L., et al., "I-R Laser: A New Therapy in Rhino-Sino-Nasal Bronchial Syndrome with Asthmatic Component," American Society for Laser Medicine and Surgery Abstracts, p. 74, 1993, 1 page.
Wizeman W., et al., "A Computer Model of Thermal Treatment of Airways by Radiofrequency (RF) Energy Delivery," American Thoracic Society Annual Meeting, 2007, 1 page.
International Search Report and Written Opinion for corresponding International Application No. PCT/US2013/041190, mailed Sep. 6, 2013, 11 pages.

* cited by examiner

ELECTRODES FOR TISSUE TREATMENT

CROSS-REFERENCE TO RELATED APPLICATIONS

This application claims the benefit of priority from U.S. Provisional Application No. 61/675,244, filed on Jul. 24, 2012, the entirety of which is incorporated by reference herein.

TECHNICAL FIELD

Embodiments of the present disclosure relate generally to devices and methods for treating tissue in a cavity or passageway of a body. More particularly, embodiments of the present disclosure relate to devices and methods employing electrodes for treating tissue in an airway of a body, among other things.

BACKGROUND

The anatomy of a lung includes multiple airways. As a result of certain genetic and/or environmental conditions, an airway may become fully or partially obstructed, resulting in an airway disease such as emphysema, bronchitis, chronic obstructive pulmonary disease (COPD), and asthma. Certain obstructive airway diseases, including, but not limited to, COPD and asthma, are reversible. Treatments have accordingly been designed in order to reverse the obstruction of airways caused by these diseases.

One treatment option includes management of the obstructive airway diseases via pharmaceuticals. For example, in a patient with asthma, inflammation and swelling of the airways may be reversed through the use of short-acting bronchodilators, long-acting bronchodilators, and/or anti-inflammatories. Pharmaceuticals, however, are not always a desirable treatment option because in many cases they do not produce permanent results, or patients are resistant to such treatments or simply non-compliant when it comes to taking their prescribed medications.

Accordingly, more durable/longer-lasting and effective treatment options have been developed in the form of energy delivery systems for reversing obstruction of airways. Such systems may be designed to contact an airway of a lung to deliver energy at a desired intensity for a period of time that allows for the airway tissue (e.g., airway smooth muscle, nerve tissue, etc.) to be altered and/or ablated. However, energy delivery through these systems to the airway tissue is not always uniform due to the contact between the systems and the tissue. Uniform delivery of energy to the airway tissue is important for enabling consistent treatment and lowering the impedance level of the tissue. There is accordingly a need for an energy delivery system that enables uniform contact between the system and the tissue of an airway.

SUMMARY OF THE DISCLOSURE

In accordance with the present disclosure, energy delivery devices and methods of use are disclosed. The energy delivery device may include an elongate member having a proximal end and a distal end, and an energy emitting portion coupled to the distal end of the elongate member. The energy emitting portion may be configured to transition between a first, collapsed configuration and a second, expanded configuration. In addition, the energy emitting portion may include a plurality of legs forming a basket, such that when the energy emitting portion is in the second, expanded configuration a central portion of at least one of the legs includes a substantially straight or linear configuration.

Embodiments of the energy delivery device may include the following features either alone or in combination: the central portion of the at least one leg may be between proximal and distal portions of the at least one leg, and the central portion may be stiffer than each of the proximal and distal portions; the central portion may include a modulus of elasticity that is greater than a modulus of elasticity of each of the proximal and distal portions; the central portion may include a cross-section dimension that is larger than a corresponding cross-section dimension of both the proximal and distal portions; at least a portion of the central portion may be surrounded by one of a hypotube or a heat shrink tube; at least one piece of material may be attached to a radially inner surface of the central portion, and the at least one piece of material may be substantially the same length as the length of the central portion, such that the at least one piece of material may include a first material, and the central portion may include a second material different from the first material; the central portion may include a folded configuration; the central portion of the at least one leg may be between proximal and distal portions that are curved in the second, expanded configuration; and the central portion of at least one leg may include a plurality of layers formed by at least two angled bends in the leg.

Additional objects and advantages of the disclosure will be set forth in part in the description which follows, and in part will be obvious from the description, or may be learned by practice of the disclosure. The objects and advantages of the disclosure will be realized and attained by means of the elements and combinations particularly pointed out in the appended claims.

The accompanying drawings, which are incorporated in and constitute a part of this specification, illustrate several embodiments of the present disclosure and together with the description, serve to explain the principles of the invention.

DESCRIPTION OF THE EMBODIMENTS

Reference will now be made in detail to exemplary embodiments of the present disclosure, examples of which are illustrated in the accompanying drawings. Wherever possible, the same reference numbers will be used throughout the drawings to refer to the same or like parts.

Embodiments of the present disclosure relate to devices and methods for applying energy to tissue within a wall or cavity of a body. More particularly, embodiments of the present disclosure relate to devices and methods for applying energy to tissue in the airway of a lung in order to treat reversible obstructive airway diseases including, but not limited to, COPD and asthma. It should be emphasized, however, that embodiments of the present disclosure may also be utilized in any procedure where heating of tissue is required, such as, for example cardiac ablation procedures.

Figure 1:
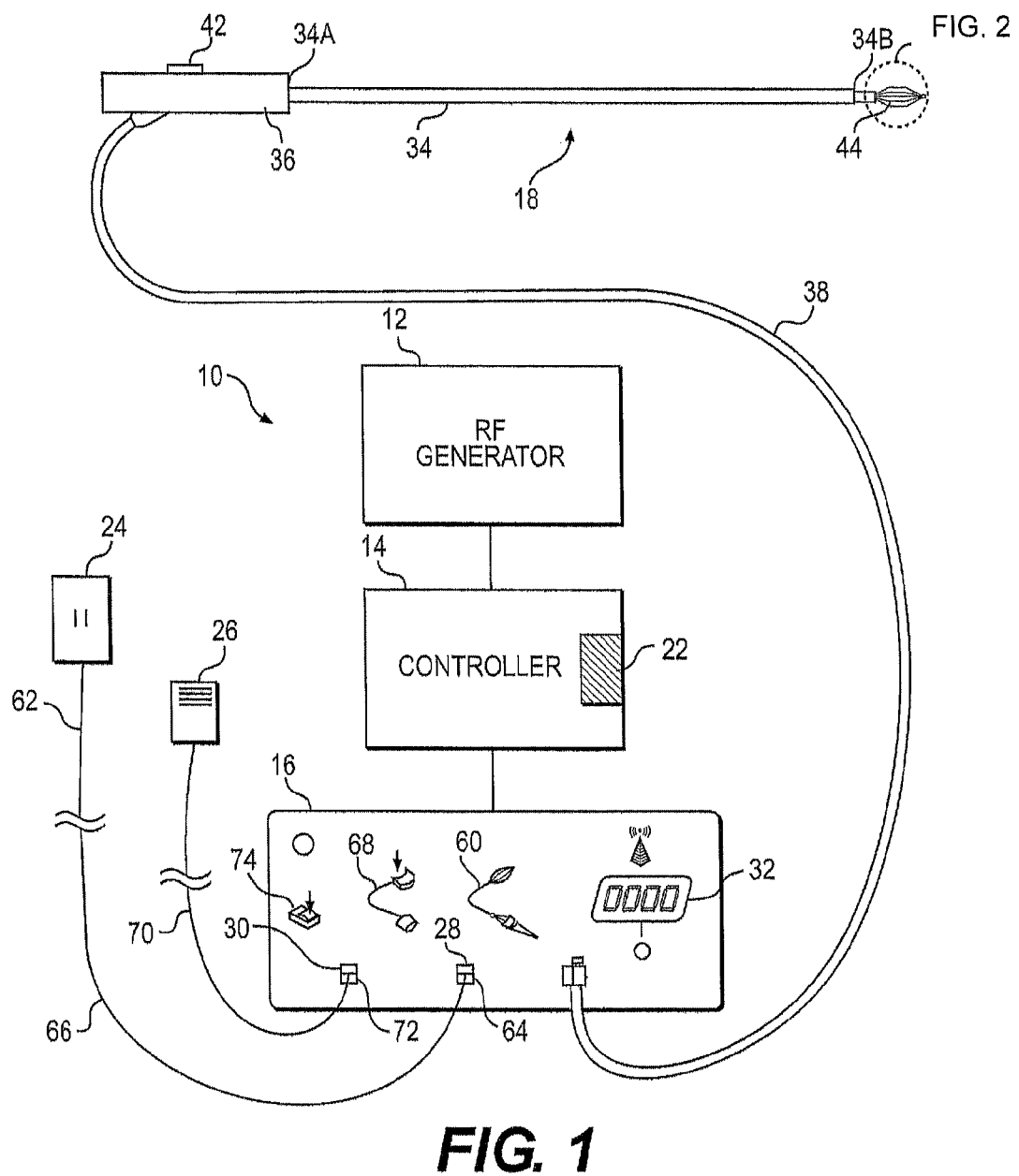
FIG. 1 is a schematic view of a system for delivering energy to tissue within a cavity or passageway of a body.

FIG. 1 illustrates a system for delivering energy 10, in accordance with a first embodiment of the present disclosure. The system may include an energy generator 12, a controller 14, a user interface surface 16, and an energy delivery device 18. Energy generator 12 may be any suitable device configured to produce energy for heating and/or maintaining tissue in a desired temperature range. In one embodiment, for example, energy generator 12 may be an RF energy generator. The RF energy generator may be configured to emit energy at specific frequencies and for specific amounts of time in order to reverse obstruction in an airway of a lung.

In certain obstructive airway diseases, obstruction of an airway may occur as a result of narrowing due to airway smooth muscle contraction. Accordingly, in one embodiment, energy generator 12 may be configured to emit energy that reduces the ability of the smooth muscle to contract, increases the diameter of the airway by debulking, denaturing, and/or eliminating the smooth muscle or nerve tissue, and/or otherwise alters airway tissue or structures. That is, energy generator 12 may be configured to emit energy capable of killing smooth muscle cells or nerve tissue, preventing smooth muscle cells or nerve tissue from replicating, and/or eliminating smooth muscle or nerve tissue by damaging and/or destroying the smooth muscle or nerve tissue.

More particularly, energy generator 12 may be configured to generate energy with a wattage output sufficient to maintain a target tissue temperature in a range of about 60 degrees Celsius to about 80 degrees Celsius. In one embodiment, for example, energy generator may be configured to generate RF energy at a frequency of about 400 kHz to about 500 kHz and for treatment cycle durations of about 5 seconds to about 15 seconds per treatment cycle. Alternatively, the duration of each treatment cycle may be set to allow for delivery of energy to target tissue in a range of about 125 Joules of RF energy to about 150 Joules of energy. In one embodiment, for example, when a monopolar electrode is used, the duration of treatment may be about 10 seconds, and the target tissue temperature may be about 65 degrees Celsius. In another embodiment, when a bipolar electrode is used, the duration of treatment may be about 2 to 3 seconds, with the target tissue temperature being approximately 65 degrees Celsius.

Energy generator 12 may further include an energy operating mechanism 26. Energy operating mechanism 26 may be any suitable automatic and/or user operated device in operative communication with energy generator 12 via a wired or wireless connection, such that energy operating mechanism 26 may be configured to enable activation of energy generator 12. Energy operating mechanism 26 may therefore include, but is not limited to, a switch, a pushbutton, or a computer. The embodiment of FIG. 1, for example, illustrates that energy operating mechanism 26 may be a footswitch 26. Footswitch 26 may include a conductive cable 70 coupled to a proximal coupler 72 which is configured to be electrically coupled to an interface coupler 30 disposed on user interface surface 16.

Energy generator 12 may be coupled to controller 14. Controller 14 may include a processor 22 configured to receive information feedback signals, process the information feedback signals according to various algorithms, produce signals for controlling the energy generator 12, and produce signals directed to visual and/or audio indicators. For example, processor 22 may include one or more integrated circuits, microchips, microcontrollers, and microprocessors, which may be all or part of a central processing unit (CPU), a digital signal processor (DSP), an analogy processor, a field programmable gate array (FPGA), or any other circuit known to those skilled in the art that may be suitable for executing instructions or performing logic operations. That is, processor may include any electric circuit that may be configured to perform a logic operation on at least one input variable. In one embodiment, for example, processor 22 may be configured use a control algorithm to process a temperature feedback signal and generate control signals for energy generator 12. Alternative or additional control algorithms and system components that may be used in conjunction with processor 22 may be found in U.S. Pat. No. 7,104,987 titled CONTROL SYSTEM AND PROCESS FOR APPLICATION OF ENERGY TO AIRWAY WALLS AND OTHER MEDIUMS, issued Sep. 12, 2006, and in U.S. Patent Application Publication No. 2009/0030477 titled SYSTEM AND METHOD FOR CONTROLLING POWER BASED ON IMPEDANCE DETECTION, SUCH AS CONTROLLING POWER TO TISSUE TREATMENT DEVICES, published on Jan. 29, 2009, each of which is incorporated by reference herein in its entirety.

Controller 14 may additionally be coupled to and in communication with user interface 16. The embodiment of FIG. 1 illustrates that controller 14 may be electrically coupled to user interface 16 via a wire connection. In alternative embodiments, however, controller 14 may be in wireless communication with user interface 16. User interface 16 may be any suitable device capable of providing information to an operator of the energy delivery system 10. Accordingly, user interface 16 may be configured to operatively couple to each of the components of energy delivery system 10, receive information signals from the components, and output at least one visual or audio signal to a device operator in response to the information received. The surface of user interface 16 may therefore include, but is not limited to, at least one switch 74, a digital display 32, visual indicators, audio tone indicators, and/or graphical representations of components of the energy delivery system 60, 68. Embodiments of user interface 16 may be found in U.S. Patent Application Publication No. 2006/0247746 A1 titled CONTROL METHODS AND DEVICES FOR ENERGY DELIVERY, published Nov. 2, 2006, which is incorporated by reference herein in its entirety.

FIG. 1 illustrates that user interface 16 may be coupled to energy delivery catheter 18. The coupling may be any suitable medium enabling distribution of energy from energy generator 12 to energy deliver device 18, such as, for example, a wire or a cable 38. Energy delivery device 18 may include an elongate member 34 having a proximal end 34A and a distal end 34B. Elongate member 34 may be any suitable longitudinal device configured to be inserted into a cavity and/or passageway of a body. Elongate member 34 may further include any suitable stiff or flexible material configured to enable movement of energy delivery device 18 through a cavity and/or passageway in a body. In one embodiment, for example, elongate member 34 may be sufficiently flexible to enable elongate member to conform to the cavity and/or passageway through which it is inserted.

Elongate member 34 may be any suitable size, shape, and or configuration such that elongate member 34 may be configured to pass through a lumen of a bronchoscope. Elongate member may be solid or hollow. In one embodiment, for example, elongate member 34 may include one or more lumens or internal channels (not shown) for the passage of an actuation/pull wire 50 (as shown) and/or a variety of surgical equipment, including, but not limited to, imaging devices and tools for irrigation, insufflation, vacuum suctioning, biopsies, and drug delivery. Elongate member 34 may further include an atraumatic exterior surface having a rounded shape and/or coating. The coating be any coating known to those skilled in the art enabling ease of movement of energy delivery device 18 through a passageway and/or cavity within a body. Coating may therefore include, but is not limited to, a lubricious coating and/or an anesthetic.

FIG. 1 further illustrates that an energy emitting portion 44 may be attached to distal end 34B of elongate member 34. Energy emitting portion 44 may be permanently or removably attached to distal end 34B of elongate member. In one embodiment, for example, energy emitting portion 44 may be permanently or removably attached to elongate member 34 via a flexible junction enabling movement of energy emitting portion 44 relative to distal end 34B of elongate member 34. Embodiments of a junction may be found, for example, in U.S. Patent Application Publication No. 2006/0247618 A2 titled MEDICAL DEVICE WITH PROCEDURE IMPROVEMENT FEATURES, published Nov. 2, 2006, which is incorporated by reference herein in its entirety.

Figure 2:
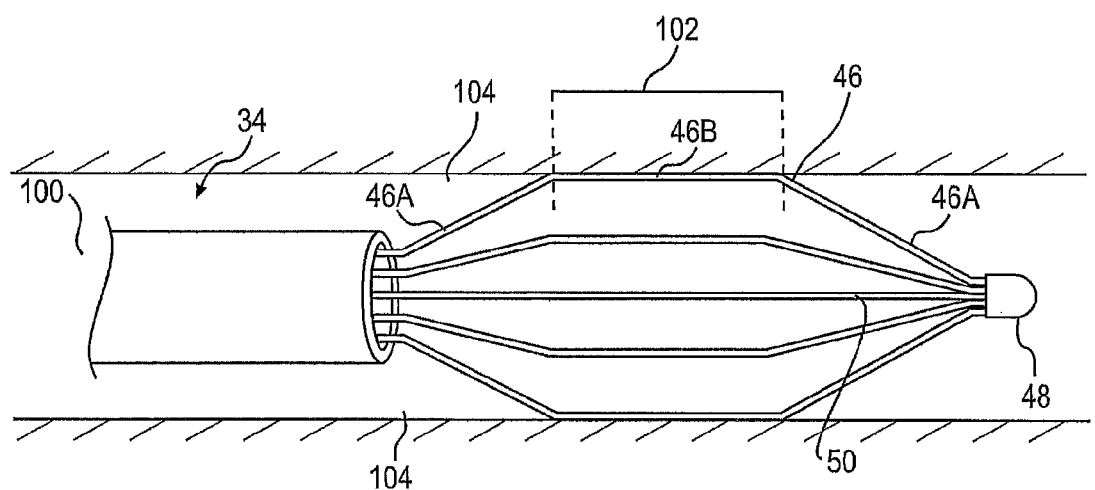
FIG. 2 is an enlarged view of a distal portion of a therapeutic energy delivery device, according to a first embodiment of the present disclosure.

Energy emitting portion 44 may be any suitable device configured to emit energy from energy generator 12. In addition, as illustrated in FIG. 2, energy emitting portion 44 may include a contact region 102 that may be configured to contact tissue 104 within a cavity and/or passageway 100 of a body. The contact region 102 may include at least a portion that is configured to emit energy from energy generator 12. Energy emitting portion 44 may further be a resilient member configured to substantially maintain a suitable size, shape, and configuration that corresponds to a size of a cavity and/or passageway in which energy delivery device 18 is inserted.

In one embodiment, for example, energy emitting portion 44 may be an expandable member. The expandable member may include a first, collapsed configuration (not shown) and a second, expanded configuration (FIG. 2). The expandable member may include any size, shape, and/or configuration, such that in the second, expanded configuration, the contact region may be configured to contact tissue in a cavity and/or passageway of a body. The expandable member of energy emitting portion 44 may be any suitable expandable member known to those skilled in the art including, but not limited to, a balloon or cage. In one embodiment, as illustrated in FIGS. 1 and 2, energy emitting portion 44 may include an expandable basket having a plurality of legs 46. The plurality of legs 46 may be configured to converge at an atraumatic distal tip 48 of energy delivery device 18.

Energy emitting portion 44 may further include at least one electrode. The at least one electrode may be any suitable electrode known to those skilled in the art configured to emit energy. The at least one electrode may be located along the length of at least one of the plurality of legs 46 and may include at least a portion of the contact region of energy emitting portion 44. Accordingly, the at least one electrode may include, but is not limited to, a band electrode or a dot electrode. Alternatively, the embodiment of FIG. 1 illustrates that at least one leg 46 of the energy emitting portion is made up of a single, elongate electrode 46. In one embodiment, for example, the elongate electrode 46 may have an electrical insulator material. In addition, at least a portion of the electrode 46 may be exposed, forming an active region for delivering energy to tissue.

As previously discussed, and illustrated in FIGS. 1 and 2, each of the plurality of legs 46 of energy emitting portion may be configured to form an expandable basket-type shape when in the second, expanded configuration. Accordingly, upon expansion of energy emitting portion 44, each of the plurality of legs 46 may be configured to bow radially outward from a longitudinal axis of energy delivery device 18. A central portion of each leg 46 may be configured to be the portion of the leg 46 that is the greatest distance from the longitudinal axis when the energy emitting portion 44 is in its second, expanded configuration. In some embodiments, the central portion of at least one leg 46 may form a rounded configuration upon expansion of energy emitting portion 44. Alternatively, as illustrated in FIGS. 2 and 3, the central portion 46B of at least one leg 46 may be configured to maintain a substantially straight or linear configuration upon expansion of energy emitting portion 44, such that energy delivery device 18 may be configured to provide uniform and controlled energy delivery to tissue in a cavity and/or passageway within a body, and such that energy delivery device 18 may be configured to provide controlled tissue to leg 46 contact at all times regardless of the size of the cavity and/or passageway.

Leg 46 may be configured to maintain the substantially flat configuration at central portion 46B as a result of mechanical properties of leg 46. For example, in one embodiment central portion 46B may have a higher modulus of elasticity than proximal and distal portions 46A of leg 46. That is, in some embodiments, central portion 46B may include a stiffer material than proximal and distal portions 46A. Alternatively, or in addition, in another embodiment, central portion 46B may have a higher moment of inertia than proximal and distal portions 46A of leg 46. The higher moment of inertia may be achieved, for example, by configuring central portion 46B to have a larger cross-sectional width and/or thickness than the proximal and distal portions 46A of leg 46.

Central portion 46B of leg 46 may accordingly be any suitable size (e.g., length), shape, and/or configuration that maintains a substantially straight configuration. In some embodiments, for example, each leg 46 may include a central portion having a substantially similar central portion 46B. Alternatively, in other embodiments, the central portion 46B of each leg 46 may vary. The size, shape, and/or configuration of the central portion 46B may be determined based on multiple factors including, but not limited to, the location of treatment, desired treatment energy level, duration of treatment, and size of body lumen.

Figure 3:
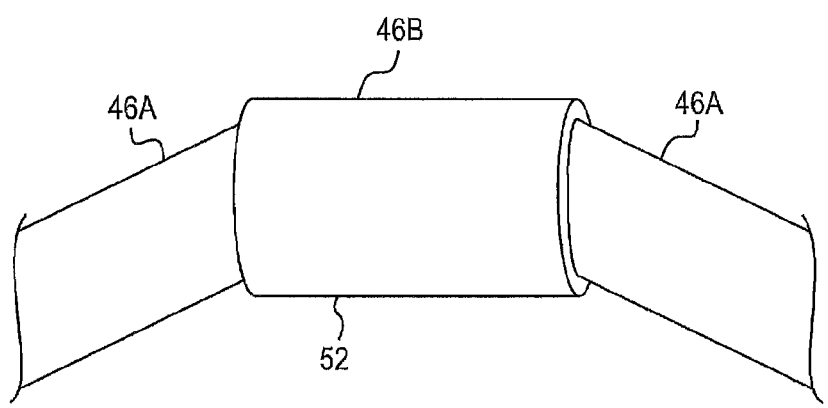
FIG. 3 is an enlarged view of an electrode of the therapeutic energy delivery device of FIG. 2.

FIG. 3 illustrates an example of a portion of a leg 46 of an expanded energy emitting portion 44 according to a first embodiment of the present disclosure. As illustrated in FIG. 3, central portion 46B may be configured to have a higher modulus of elasticity and/or a higher moment of inertia than proximal and distal portions 46A of leg 46. Leg 46 may include any suitable material known to those skilled in the art configured to emit energy and resiliently bow outward. Suitable materials may include, but are not limited to, metals and metal alloys. In one embodiment, for example, leg 46 may include stainless steel or nitinol.

Leg 46 may further include a stiffer material at central portion 46B relative to remaining portions of leg 46. In one embodiment, for example, proximal and distal portions 46A of leg 46 may be permanently or removably connected to central portion 46B. In addition, proximal and distal portions 46A of leg 46 may include a metal or metal alloy having a lower modulus of elasticity than the metal or metal alloy of central portion 46B. Proximal and distal portions 46A of leg 46 may include the same or different materials, with the material determination of each of the proximal, distal, and central portions of leg 46 being determined by the desired shape of energy emitting portion 44 when energy emitting portion 44 is in the second, expanded configuration.

In an alternative embodiment, proximal, distal and central portions of leg 46 may include a continuous piece of metal or metal alloy. Central portion 46B may additionally be at least partially surrounded by a layer of material having a higher modulus of elasticity than the metal or metal alloy. The surrounding material may be any suitable material configured to maintain central portion 46B in a substantially straight configuration when energy emitting portion 44 is expanded. Suitable materials for the surrounding layer may include, but are not limited to, polymers, polymer alloys, metals, and metal alloys. In one embodiment, as illustrated in FIG. 3, central portion 46B may be at least partially surrounded by a hypotube 52. Alternatively, central portion 46B may be at least partially surrounded by a PEEK tubing and/or a PEEK heat shrink tubing. Central portion 46B may be configured, however, such that at least a portion of the contact region 102 of leg 46 is not surrounded by any non-conductive material.

Figure 4:
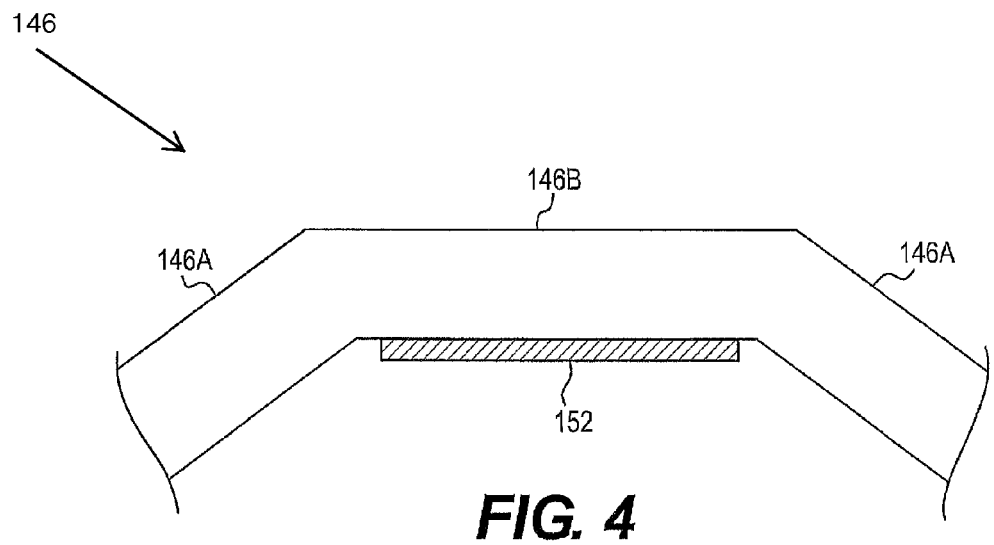
FIG. 4 is an enlarged view of an electrode of a therapeutic energy delivery device, according to a second embodiment of the present disclosure.

FIG. 4 illustrates an example of a portion of a leg 146 of an expanded energy emitting portion 44 according to a second embodiment of the present disclosure. Similar to the embodiment of FIG. 3, proximal portion 146A, central portion 146B, and distal portion 146A may be different pieces of material connected by any suitable means known to those skilled in the art. Alternatively, as illustrated in FIG. 4, leg 146 may be a single piece of material. At least one piece or layer of material 152 may be attached to at least one surface of the central portion 1466 of leg 146. The at least one piece of material 152 may include a length that is substantially the same as a length of central portion 146B of leg 146. Piece 152 also may have a cross-sectional size that approximates a width of leg 146, if leg 146 is flat, or a diameter of leg 146 if leg 146 is round. Accordingly, the at least one piece of material 152 may act as a stiffener for central portion 146B of leg 146.

FIG. 4 illustrates that the at least one piece of material 152 may be attached to a bottom surface of central portion 146B of leg 146. In alternative embodiments, however, the at least one piece of material may be attached to any surface (e.g., side, top, and/or bottom) such that central portion 146B of leg 146 may be configured to maintain a substantially straight configuration when energy emitting portion 44 is in the second, expanded configuration.

The at least one piece of material 152 may further be any suitable material known to those skilled in the art. Piece 152 may be conductive, especially if positioned on an outer tissue contacting surface of leg 146, or non-conductive, especially if positioned on an inner non-tissue contacting surface of leg 146. Suitable materials may include, but are not limited to, polymers and polymer alloys such as plastics, PEEK, and PET; and metals and metal alloys such as stainless steel. Similar to the embodiment of FIG. 3, the at least one piece of material 152 may be chosen based on multiple factors, including, but not limited to, the desired stiffness of central portion 146B and the shape, size, and/or configuration of central portion 146B. In the embodiment of FIG. 4, for example, the at least one piece of material 152 may be a stainless steel ribbon wire.

Moreover, the at least one piece of material 152 may be attached to the at least one surface of central portion 146B of leg 146 via any suitable means known to those skilled in the art. Suitable attachment means may enable the at least one piece of material 152 to be permanently or removably attached to central portion 146B of leg 146. Accordingly, suitable attachment means may include, but are not limited to, welding, gluing, soldering, or any other adhesive method known to those skilled in the art. In the embodiment of FIG. 4, for example, the at least one piece of material 152 may be attached to the at least one surface of central portion 146B by laser welding. In some embodiments, a coating, such as PET shrink may additionally be placed onto the at least one surface of central portion 146B of leg 146 in order to enhance attachment of the at least one piece of material 152 with central portion 146B. Similar to the embodiment of FIG. 3, however, central portion 146B may be configured such that at least a portion of the tissue contact region 102 of leg 146 is not surrounded by any non-conductive material.

Figure 5A:
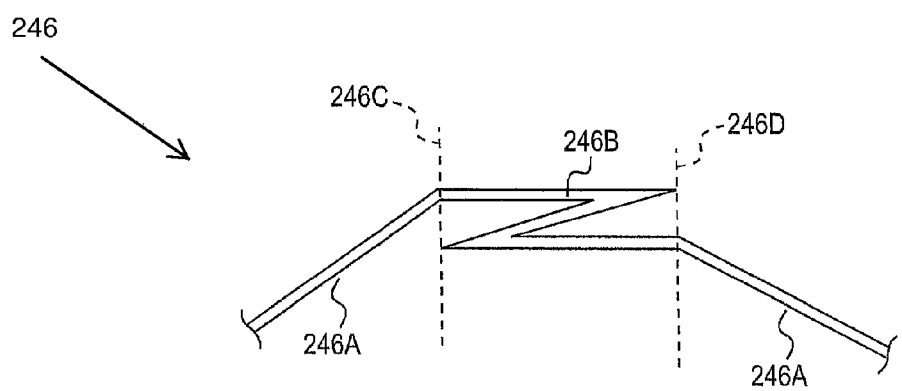
FIG. 5A is an enlarged view of an electrode of a therapeutic energy delivery device, according to a third embodiment of the present disclosure.
Figure 5B:
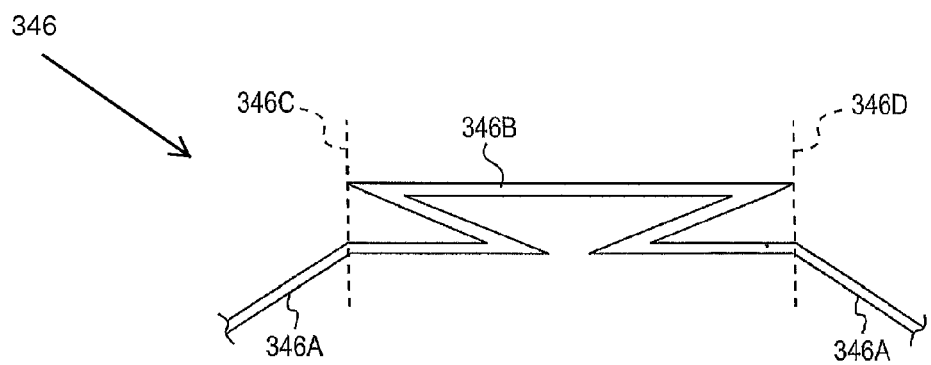
FIG. 5B is an enlarged view of an electrode of a therapeutic energy delivery device, according to a fourth embodiment of the present disclosure.

FIGS. 5A and 5B illustrate further examples of legs 246, 346 of expanded energy emitting portions 44 according to third and fourth embodiments, respectively, of the present disclosure. As previously discussed, one means of stiffening the central portion of a leg includes creating a cross-sectional width and/or thickness that is larger than the cross-sectional width and/or thickness of the proximal and distal portions of the leg. As illustrated in FIGS. 5A and 5B, this may be accomplished by folding the leg in a manner such that the central portion of leg is provided with a thicker cross-section than that of the proximal and distal portions.

Similar to the embodiment of FIG. 4, legs 246, 346 may include a single piece of material to be folded. Alternatively, however, central section 246B, 346B may include at least one different piece of material than that of proximal and distal portions 246A, 346A of leg 246, 346. For example, in one embodiment, the central portion may include multiple pieces of material connected to each other and to the proximal and distal portions of the leg in a hinge-like manner in order to facilitate folding.

Central portion 246B, 346B of leg may further be folded in any suitable configuration known to those skilled in the art such that the folded central portion may be configured to maintain a substantially straight configuration upon expansion of energy emitting portion 44. As illustrated in FIGS. 5A and 5B, folding of central portion 246B, 346B may be symmetrical or non-symmetrical about a plane perpendicular to central portion 246B, 346B at a midpoint of central portion 246B, 346B. For example, FIG. 5A illustrates a non-symmetrical fold of central portion 246B. That is, upon folding of central portion 246B, proximal and distal portions 246A of leg 246 are offset from one another. In the alternative, FIG. 5B illustrates a symmetrical fold, such that folding of central portion 346B creates a configuration of leg 346 where both the proximal and distal portions 346A of leg 346 are aligned radially.

FIGS. 5A and 5B illustrate that central portion 246B, 346B may be folded in order to form a plurality of layers of leg 246, 346. Each central portion 246B, 346B may therefore include at least two angled bends. The at least two angled bends may form a z-shape. Accordingly, at least certain embodiments of legs with central portions having folded configurations each include at least one z-shape. For example, FIG. 5A illustrates a folded central portion 246B with one z-shape. Alternatively, FIG. 5B illustrates a folded central portion 346B with two z-shapes. Moreover, while the present disclosure describes the at least one z-shape in the leg 246, 246 as being "folded," it should be emphasized that the at least one z-shape in the leg 246, 346 may be formed by any suitable means known to those skilled in the art, including, but not limited to stamping and/or bending of leg 246, 346.

Folded legs 246, 346 may additionally include retaining means for maintaining central portion 246B, 346B in the desired folded configuration. The retaining means may be any suitable means configured to prevent central portion 246B, 346B from unfolding. Suitable retaining means may include, but are not limited to, adhesives, tubing, and materials for tying down end portions 246C, 246D, 346C, 346D of the fold. In one embodiment, for example, central portion may be retained in PET shrink material, with the PET shrink material covering all or none of proximal and distal portions of leg. As with the prior disclosed embodiments, however, central portion 246B, 346B may be configured such that at least a portion of contact region 102 of leg 246, 346 may not be surrounded by a non-conductive material.

With reference back to FIGS. 1 to 3, the plurality of legs 46 include at least one electrode. The at least one electrode may be monopolar or bipolar. The embodiment of FIG. 1 illustrates an energy emitting portion 44 including monopolar electrodes. Accordingly, the embodiment of FIG. 1 further includes a return electrode component 62 configured to complete an electrical energy emission or patient circuit between energy generator 12 and a patient (not shown). Return electrode component 62 may include a conductive pad 24, a proximal coupler 64 and a conductive cable 66 extending between and in electrical communication with conductive pad 24 and proximal coupler 64.

Conductive pad 24 may include a conductive adhesive surface configured to removably stick to a patient's skin. In addition, conductive pad 24 may include a surface area having a sufficient size in order to alleviate burning or other injury to the patient's skin that may occur in the vicinity of the conductive pad 24 during energy emission. Moreover, proximal coupler 64 may be configured to couple to an interface coupler 28 on user interface surface 16. As illustrated in FIG. 1, interface coupler 28 may be disposed adjacent a graphical representation 68 of the electrode return 62 on the user interface surface 16, such that user interface surface 16 may be configured to provide at least a visual indicator in relation to return electrode component 62.

Energy delivery device 18 may further include a handle 36. Handle 36 may be any suitable handle known to those skilled in the art configured to enable a device operator to control movement of energy delivery device 18 through a patient. In addition, in some embodiments, handle 36 may further be configured to control expansion of energy emitting portion 44.

In one embodiment, for example, a push rod, cable, or wire may be located within handle and may extend through elongate member, connecting to a proximal end of energy emitting portion. Actuation of handle may allow for distal movement of push rod, cable, or wire, which may exert a distal force on proximal end of energy emitting portion 44. The force on proximal end of energy emitting portion 44 may cause each of the plurality of legs 46 to bow radially outward, thereby expanding energy emitting portion. Alternatively, as illustrated in FIG. 2, a pull wire, rod, or cable 50 may extend from handle 36 and connect to distal tip 48. Actuation of handle 36 may exert a proximal force of pull wire, rod, or cable 50, thereby causing the plurality of legs 46 to bow outward and expand energy emitting portion 44.

Handle 36 may accordingly include an actuator mechanism, including, but not limited to, a squeeze handle, a foot pedal, a switch, a push button, a thumb wheel, or any other known suitable actuation device. The embodiment of FIG. 1, for example, illustrates that the actuator mechanism may be a sliding actuator 42. Sliding actuator 42 may be connected to pull wire 50 and may be any suitable device known to those skilled in the art configured to move along handle 36 in both the proximal and distal directions. Sliding actuator 42 may additionally include at least one of a stop and/or a locking mechanism. In one embodiment, for example, sliding actuator 42 may be ratcheted. Alternatively, sliding actuator may be configured to slide freely in both the proximal and distal directions until being acted on by one of the stop and/or locking mechanism. A further embodiment of handle 36 may be found in U.S. Patent Application Publication No. 2009/0018538 titled SYSTEMS AND METHODS FOR DELIVERING ENERGY TO PASSAGEWAYS IN A PATIENT, published on Jan. 15, 2009, which is incorporated by reference herein in its entirety.

Energy delivery device 18 may further include at least one sensor (not shown) configured to be in wired or wireless communication with the display and/or indicators on user interface surface 16. In one embodiment, for example, the at least one sensor may include a wire extending through elongate member 34 and handle 36, and being operatively connected to cable 38.

The at least one sensor may be configured to sense tissue temperature and/or impedance level. In one embodiment, for example, energy emitting portion 44 may include at least one temperature sensor in the form of a thermocouple. Embodiments of the thermocouple may be found in U.S. Patent Application Publication No. 2007/0100390 A1 titled MODIFICATION OF AIRWAYS BY APPLICATION OF ENERGY, published May 3, 2007, which is incorporated by reference herein in its entirety.

In addition, the at least one sensor may be configured to sense functionality of the energy delivery device. That is, the at least one sensor may be configured to sense the placement of the energy delivery device within a patient, whether components are properly connected, whether components are properly functioning, and/or whether components have been placed in a desired configuration. In one embodiment, for example, energy emitting portion 44 may include a pressure sensor or strain gauge for sensing the amount of force energy emitting portion 44 exerts on tissue in a cavity and/or passageway in a patient. The pressure sensor may be configured to signal energy emitting portion 44 has been expanded to a desired configuration such that energy emitting portion 44 may be prevented from exerting a damaging force on surrounding tissue or the device 44 (e.g., electrode inversion) or not enough force indicating that improved tissue electrode contact is needed for improved performance. Accordingly, the at least one sensor may be placed on any suitable portion of energy delivery device including, but not limited to, on energy emitting portion 44, elongate member 34, and/or distal tip 48.

In addition, energy delivery device 18 may include at least one imaging device (not shown) located on one of the energy emitting portion 44, elongate member 34, and/or distal tip 48. The imaging device may include a camera or any other suitable imaging device known to those skilled in the art configured to transmit images to an external display. The energy delivery device may additionally include at least one illumination source. The illumination source may be integrated with the imaging device or controller, or a separate structure attached to one of the energy emitting portion 44, elongate member 34, and/or distal tip 48. The illumination source may provide light at a wavelength for visually aiding the imaging device. Alternatively, or in addition, the illumination source may provide light at a wavelength that allows a device operator to differentiate tissue that has been treated by the energy delivery device from tissue that that not been treated.

Additional embodiments of the imaging or mapping device may be found in U.S. Patent Application Publication Nos. 2006/0247617 A1 titled ENERGY DELIVERY DEVICES AND METHODS, published Nov. 2, 2006; 2007/0123961 A1 titled ENERGY DELIVERY AND ILLUMINATION DEVICES AND METHODS, published May 31, 2007; and 2010/0268222 A1 titled DEVICES AND METHODS FOR TRACKING AN ENERGY DEVICE WHICH TREATS ASTHMA, published Oct. 21, 2010, each of which are incorporated by reference herein in its entirety.

Other embodiments of the present disclosure will be apparent to those skilled in the art from consideration of the specification and practice of the present disclosure disclosed herein. It is intended that the specification and examples be considered as exemplary only, with a true scope and spirit of the present disclosure being indicated by the following claims.

What is claimed is:

1. An energy delivery device, comprising:
   an elongate member having a proximal end and a distal end; and
   an energy emitting portion coupled to the distal end of the elongate member, wherein the energy emitting portion is configured to transition between a first, collapsed configuration and a second, expanded configuration;
   wherein the energy emitting portion includes a plurality of legs forming a basket, wherein a central longitudinal axis passes through a radial center of the basket, and wherein, when the energy emitting portion is in the second, expanded configuration, a central portion of at least one of the plurality of legs includes (a) a first substantially straight section that is positioned at a first distance from the central longitudinal axis when in the second, expanded configuration, and (b) a second substantially straight section that is positioned at a second distance from the central longitudinal axis when in the second, expanded configuration, wherein the first distance and the second distance are different, wherein the central portion of the at least one leg further includes a connecting portion that extends proximally from a distal end of the first substantially straight section to a proximal end of the second substantially straight section, and wherein the first substantially straight section and the second substantially straight section are spaced apart from one another by a third distance in the first, collapsed configuration, and by a fourth distance in the second, expanded configuration, wherein the fourth distance is larger than the third distance.

2. The energy delivery device of claim 1, wherein the central portion of the at least one leg is between proximal and distal portions of the at least one leg, and wherein the central portion is stiffer than each of the proximal and distal portions.

3. The energy delivery device of claim 2, wherein the central portion of the at least one leg includes a modulus of elasticity that is greater than a modulus of elasticity of each of the proximal and distal portions.

4. The energy delivery device of claim 2, wherein the central portion of the at least one leg includes a cross-section dimension that is larger than a corresponding cross-section dimension of each of the proximal and distal portions.

5. The energy delivery device of claim 2, wherein the proximal portion extends distally from the distal end of the elongate member and radially outward from the central longitudinal axis.

6. The energy delivery device of claim 5, wherein the first substantially straight section of the central portion extends distally from a distal end of the proximal portion of the at least one leg.

7. The energy delivery device of claim 1, wherein the central portion includes a folded configuration.

8. The energy delivery device of claim 1, wherein the first substantially straight section is substantially parallel to the second substantially straight section.

9. The energy delivery device of claim 1, wherein a longitudinal axis of the connecting portion is substantially parallel to a longitudinal axis of each of the first substantially straight section and the second substantially straight section in the first, collapsed configuration, and intersects the longitudinal axis of each of the first substantially straight section and the second substantially straight section, in the second, expanded configuration.

10. The energy delivery device of claim 9, wherein the first substantially straight section, the connecting portion, and the second substantially straight section form a z-shape in the second, expanded configuration.

11. An energy delivery device, comprising:
    an elongate member having a proximal end and a distal end; and
    an energy emitting portion coupled to the distal end of the elongate member, wherein the energy emitting portion is configured to transition between a first, collapsed configuration and a second, expanded configuration;
    wherein the energy emitting portion includes a plurality of legs forming a basket, wherein a central longitudinal axis passes through a radial center of the basket, wherein each leg of the plurality of legs includes a proximal portion extending radially outward away from the central longitudinal axis, a central portion extending distally from a distal end of the of the proximal portion, and a distal portion extending distally from the central portion and radially inward toward the central longitudinal axis, wherein the central portion includes a first substantially straight portion, a second substantially straight portion, and third substantially straight portion, wherein the first substantially straight portion is collinear with and spaced apart from the third substantially straight portion, and the second substantially straight portion is substantially parallel to the first and third substantially straight portions, and wherein the central portion is stiffer than each of the proximal and distal portions such that when the energy emitting portion is in the second, expanded configuration the central portion includes a substantially linear configuration, and wherein the first substantially straight portion and the second substantially straight portion are spaced apart from one another by a first distance in the first, collapsed configuration, and by a second distance in the second, expanded configuration, wherein the second distance is larger than the first distance.

12. The energy delivery device of claim 11, wherein the central portion of at least one leg of the plurality of legs includes a cross-section dimension that is larger than a corresponding cross-section dimension of both the proximal and distal portions.

13. The energy delivery device of claim 11, wherein a central portion of each of the plurality of legs includes a substantially straight configuration.

14. The energy delivery device 11, wherein the central portion further includes a first connecting portion that extends proximally from a distal end of the first substantially straight portion and away from the central longitudinal axis, to a proximal end of the second substantially straight portion, and a second connecting portion that extends proximally from a distal end of the second substantially straight portion and toward the central longitudinal axis to a proximal end of the third substantially straight portion, when in the second, expanded configuration.

15. The energy delivery device of claim 14, wherein the second substantially straight portion is disposed further from the central longitudinal axis than the first substantially straight portion and the third substantially straight portion.

16. The energy delivery device of claim 15, wherein:
   a longitudinal axis of the first connecting portion is substantially parallel to a longitudinal axis of each of the first substantially straight portion and the second substantially straight portion when in the first, collapsed configuration, and intersects the longitudinal axis of each of the first substantially straight portion and the second substantially straight portion, when in the second, expanded configuration, and
   a longitudinal axis of the second connecting portion is substantially parallel to a longitudinal axis of the third substantially straight portion and the longitudinal axis of the second substantially straight portion when in the first, collapsed configuration, and intersects the longitudinal axis of each of the third substantially straight portion and the second substantially straight portion, when in the second, expanded configuration.

17. The energy delivery device of claim 16, wherein the first substantially straight portion, the first connecting portion, and the second substantially straight portion form a first z-shape, when in the second, expanded configuration, and the second substantially straight portion, the second connecting portion, and the third substantially straight portion form a second z-shape when in the second, expanded configuration, wherein the first z-shape and the second z-shape are mirror images of one another about an axis that is perpendicular to the central longitudinal axis.

* * * * *